US008552211B2

(12) United States Patent
Ueyama et al.

(10) Patent No.: US 8,552,211 B2
(45) Date of Patent: Oct. 8, 2013

(54) DRY OIL-AND-FAT SEPARATION METHOD

(75) Inventors: Koreta Ueyama, Izumisano (JP); Toshiaki Takahashi, Izumisano (JP); Kenji Murai, Izumisano (JP); Shin Yoneda, Izumisano (JP)

(73) Assignee: Fuji Oil Company, Limited, Osaka (JP)

( * ) Notice: Subject to any disclaimer, the term of this patent is extended or adjusted under 35 U.S.C. 154(b) by 142 days.

(21) Appl. No.: 13/148,090

(22) PCT Filed: Jan. 27, 2010

(86) PCT No.: PCT/JP2010/000462

§ 371 (c)(1), (2), (4) Date: Aug. 24, 2011

(87) PCT Pub. No.: WO2010/089973

PCT Pub. Date: Aug. 12, 2010

(65) Prior Publication Data

US 2011/0301372 A1 Dec. 8, 2011

(30) Foreign Application Priority Data

Feb. 6, 2009 (JP) ................................ 2009-026301

(51) Int. Cl.
*C07C 51/43* (2006.01)

(52) U.S. Cl.
USPC .......................................................... 554/211

(58) Field of Classification Search
USPC .......................................................... 554/211
See application file for complete search history.

(56) References Cited

U.S. PATENT DOCUMENTS

| | | | |
|---|---|---|---|
| 4,594,194 | A | 6/1986 | Dieffenbacher |
| 5,045,243 | A | 9/1991 | Kuwabara et al. |
| 5,556,972 | A | 9/1996 | Keulemans et al. |
| 7,727,569 | B2 | 6/2010 | Kuwabara et al. |
| 7,767,241 | B2 | 8/2010 | Kuwabara et al. |
| 2006/0165867 | A1 | 7/2006 | Kuwabara et al. |

FOREIGN PATENT DOCUMENTS

| | | | |
|---|---|---|---|
| JP | 60-101197 | | 6/1985 |
| JP | 7-98956 | | 10/1995 |
| JP | 2600010 | | 1/1997 |
| JP | 2004-123839 | | 4/2004 |
| JP | 2004123839 | * | 4/2004 |
| JP | 2005-60523 | | 3/2005 |
| WO | 2005/063952 | | 7/2005 |

OTHER PUBLICATIONS

International Search Report issued Feb. 23, 2010 in International (PCT) Application No. PCT/JP2010/000462.

International Preliminary Report on Patentability and Written Opinion issued Sep. 13, 2011 in International Application No. PCT/JP2010/000462, of which the present application is the national stage.

* cited by examiner

*Primary Examiner* — Deborah D Carr

(74) *Attorney, Agent, or Firm* — Wenderoth, Lind & Ponack, L.L.P.

(57) ABSTRACT

Disclosed is a dry oil-and-fat separation method of high yield and high separation accuracy, which uses agitation and crystallization in order to prevent problems with thickening of the crystal slurry and decreased solid/liquid separation efficiency in the crystallization/press-filtering process of dry separation of oil-and-fat containing highly crystalline SUS. In dry separation, the crystallization/press-filtering process is divided into multiple steps and repeated, to concentrate the SUS in each crystal fraction and yield SUS-rich oil and fat. Subdivision into multiple steps makes it possible to keep the crystallinity of the crystal slurry in the crystallization/press-filtering process within a range so that the crystal slurry can be transported by pump, and to increase solid/liquid separation efficiency.

7 Claims, No Drawings

DRY OIL-AND-FAT SEPARATION METHOD

TECHNICAL FIELD

The present invention relates to a dry fractionation (separation) method of an oil-and-fat containing SUS (SUS: 2-unsaturated, 1,3-disaturated glycerides, S: saturated fatty acid having 16 to 22 carbon atoms, U: unsaturated fatty acid having 18 carbon atoms).

BACKGROUND ART

Shea butter, sal fat, allanblackia fat, palm oil and an interesterified oil obtained by selectively introducing a saturated fatty acid into 1,3-positions of an oil-and-fat rich in oleic acid at 2-position of the triglyceride such as high oleic sunflower oil, contains a large amount of SUS (symmetric triglycerides) such as StOSt, POSt, and POP (St: stearic acid, O: oleic acid, P: palmitic acid). From these oils-and-fats containing SUS, various oils-and-fats for chocolate similar to cocoa butter, cocoa butter substitutes, are produced.

While the oils-and-fats can be used as it is for making confectionary such as chocolate, cream and margarine, the solvent fractionation using hexane or acetone has been widely performed so that the concentration of SUS of the crystal fraction fractionated is further increased in content.

Such a crystal fraction rich in SUS can be one of the high quality cocoa butter substitutes having high snappiness, heat resistance and shape keeping property, and a good melting speed in the mouth with a cool sensation, for chocolate.

Solvent fractionation is extremely good in the separation efficiency of fractionation into a crystal fraction and a liquid fraction. However, since a solvent is used, there are problems that the handling thereof requires sufficient attention in terms of safety and health, and that the process cost is somewhat expensive because of requirements for large-scale equipment and removal of the solvent.

For this reason, recently, a dry fractionation method which is easy and highly safe has been developed.

The dry fractionation method includes completely melting a raw material oil-and-fat by heating generally without using a solvent, cooling the molten oil-and-fat in a crystallization tank with stirring in order to crystallize the high melting point fraction, then separating the oil-and-fat into a crystal fraction and a filtrate (unsolidified low melting point fraction) by pressing and/or filtration, and this method has been merely utilized in fractionating a lauric oil-and-fat and palm oil. That is, the conventional crystallization method with stirring was not applicable to the fractionation of an oil-and-fat having a SUS content of 30% by weight or more. If such an oil-and-fat is subjected to the stirring method to obtain a fraction richer in a SUS content, it is difficult to separate the oil-and-fat into a crystal fraction and a filtrate successively. Because the crystal amount is too much and fine crystals are precipitated throughout the oil-and-fat, and thereby the entire oil-and-fat becomes too high in viscosity or is solidified and cannot be transported with a pump to the subsequent press-filtering step. This tendency is particularly remarkable in shea butter, sal fat and the like containing a large amount of StOSt, and the stirring method has been difficult to apply for these oils-and-fats.

PRIOR ART DOCUMENTS

Patent Documents

For this reason, as an alternative dry fractionation method for obtaining a crystal fraction having a high SUS content with a higher yield, stationary crystallization methods have been proposed. Patent Document 1 discloses a method of adding a stable crystal seed of β,β prime to a raw material oil-and-fat at a temperature which is 3-10° C. higher than the solidification point temperature of the oil-and-fat, crystallizing the oil-and-fat to some extent, thereafter, transferring a paste-like crystal slurry into a pressing bag, further subjecting the slurry to a stationary crystallization, and then piling the pressing bag up, and pressurizing and pressing the pressing bag with a press. In this method, however, there is a problem that a long processing time is required for crystallization and, moreover, much work and labor are necessary.

Patent Document 2 relates to a method of rapidly cooling and solidifying a completely molten raw material oil-and-fat without stirring so that unstable crystals are formed, and then leaving the crystals at a temperature which is 1 to 15° C. lower than the melting point of stable crystals so as to precipitate the particulate stable crystal, and then mechanically crushing the crystal mass into a slurry and separating the slurry with a filter press. In this method, however, there is a problem that the process is such a complicated process that a cooling apparatus for rapid cooling for solidification, a storage warehouse for obtaining stable crystals, and an apparatus for crushing the crystal mass are required and, at the same time, a long processing time is required for obtaining the stable crystals.

Patent Document 3 filed by the applicant relates to a method of pre-cooling a completely molten raw material oil-and-fat, dispensing the pre-cooled oil-and-fat into multi-stage-arranged trays, leaving the trays to a stationary crystallization by air cooling, mechanically crushing the crystals into a slurry after completion of crystallization, and separating the slurry with a press-filtering equipment. In this method, there is a problem of entrainment of the filtrate into crystals, and separation accuracy is slightly insufficient for the fractionation of an oil-and-fat containing SUS.

Patent Document 4 relates to a method obtained by improvement of the method of Patent Document 3 by the applicant, which is a method of subjecting a completely molten raw material oil-and-fat to a stationary crystallization in trays by air cooling, mechanically crushing the crystal into slurry, press-filtering the slurry, adding and mixing the molten and temperature-adjusted raw material oil-and-fat to a press cake, and press-filtering the resultant mixture again to obtain a fraction having a high SUS content. Although this method has high separation accuracy, there is a problem that the process is such slightly complicated that the air cooling facility is long and large, and the facility cost is considerably high.

In addition, as a stirring crystallization method of crystallizing an oil-and-fat having a much crystal amount, a countercurrent dry fractionation method as in Patent Document 5 has been proposed. The method includes at least two stages of dry fractionation crystallization treatment in which a second olein fraction is recirculated into a first olein fraction so that the crystal amount is reduced to make the crystal amount in a stirring crystallization in an acceptable range. However, the process is complicated and difficult to control, and at the same time, an applicable oil-and-fat is limited to palm oil, palm kernel oil, beef tallow, butter fat, fish oil and a mixture thereof, and a partially hardened oil and an interesterified oil thereof, and application to an oil-and-fat containing a much amount of StOSt is difficult.

Patent Document 1: JP 60-101197 A
Patent Document 2: JP 2005-60523 A
Patent Document 3: JP 7-98956 B
Patent Document 4: WO 2005/63952 A1
Patent Document 5: JP 2600010 B

SUMMARY OF THE INVENTION

Problems to be Solved by the Invention

An object of the present invention is to provide a dry oil-and-fat fractionation method for more easily obtaining an SUS-rich crystal fraction at a high yield in a dry fractionation of SUS-containing oil-and-fat.

Means for Solving the Problems

The applicant previously succeeded in development of a dry fractionation method having high separation accuracy by a stationary crystallization method, and subsequently, has been made efforts toward reduction in the production facility cost and production cost. Under such circumstances, the applicant intensively studied a method of overcoming a problem of an increase in viscosity of a crystal slurry in a stirring crystallization method and a method of reducing an amount of entrainment of the filtrate into crystals, and as a result, found out a method by which a SUS-rich crystal fraction is obtained easily at a high yield even by the stirring crystallization method. Thus, the present invention has been completed.

That is, a first aspect of the present invention is a method of fractionating an SUS-rich oil-and-fat by multistage fractionation, comprising concentrating SUS into a crystal fraction by dry fractionation with a stirring crystallization and a press-filtration using an oil-and-fat containing SUS as a raw material, and concentrating SUS remaining in a filtrate fraction into a crystal fraction by dry fractionation at a next stage with a stirring crystallization and a press-filtration, (SUS: 2-unsaturated, 1,3-disaturated glycerides, S: saturated fatty acid having 16 to 22 carbon atoms, U: unsaturated fatty acid having 18 carbon atoms).

A second aspect is the fractionation method according to the first aspect, wherein a crystal amount of a crystal slurry to be subjected to the press-filtration is 10 to 20% by weight as a solid fat content.

A third aspect is the fractionation method according to the first aspect, wherein a SUS content of the oil-and-fat containing SUS is 30% by weight or more, and an SUS content of the SUS-rich oil-and-fat is 60% by weight or more.

A fourth aspect is the fractionation method according to the first or second aspect, wherein SUS is substantially StOSt, (St: stearic acid, O: oleic acid).

A fifth aspect is the fractionation method according to the first or fourth aspect, wherein the oil-and-fat containing StOSt is one or more of oil-and-fat selected from a group consisting of shea butter, sal fat, allanblackia fat, and an interesterified oil obtained by selectively introducing stearic acid into 1,3-positions of an oil-and-fat rich in oleic acid at a 2-position of a triglycerides.

Effects of the Invention

In the dry fractionation method of an oil-and-fat containing SUS, the problem of an increase in viscosity of a crystal slurry at a stirring crystallization can be overcome, and it has become possible to reduce an amount of entrainment of the filtrate into the crystals. Thus, a SUS-rich crystal fraction useful in an oil-and-fat for chocolate can be obtained easily at a low cost.

BEST MODE FOR CARRYING OUT THE INVENTION

The dry fractionation method of the present invention will be explained in detail.

SUS referred to in the present invention is a triglycerides, to a 2-position of which an unsaturated fatty acid having 18 carbon atoms is bound, and to 1,3-positions of which a saturated fatty acid having 16 to 22 carbon atoms is bound. A stirring crystallization is a crystallization method of crystallizing a raw material oil-and-fat which has been molten completely by heating, while the oil-and-fat is stirred all the time from the start of cooling to the completion of crystallization. In addition, press-filtration is a method of filtrating a crystallized crystal slurry while a pressure is applied to perform solid liquid separation, and a pressed cake is a crystal fraction and a filtrate is a filtrate fraction.

The dry fractionation method according to the present invention can be typically performed by the following procedure.

1) A raw material oil-and-fat is heated to 45° C. or higher, preferably 50° C. to 70° C. to completely melt.
2) The molten oil-and-fat is cooled in a crystallization tank equipped with a stirring device and a cooling device with a coolant while stirring, thereby, crystallization is performed. The coolant temperature at that time is appropriately set for giving a crystal slurry having such flowability that the slurry can be pumpable after crystallization.
3) After completion of crystallization, the crystal slurry is pumped into a press-filtration equipment.
4) The slurry is press-filtered to separate into a crystal fraction in which SUS is concentrated, and a filtrate fraction.
5) In order to concentrate and separate SUS remaining in the filtrate fraction, the operations 1) to 4) are repeated to separate the resulting filtrate fraction into a second stage crystal fraction in which SUS is concentrated, and a second stage filtrate fraction.
6) If necessary, the operations 1) to 4) are repeated to further separate the second stage filtrate fraction into a third stage crystal fraction in which SUS is concentrated, and a third stage filtrate fraction.

Thus, SUS-rich oils-and-fats are fractionated by multiple stages, and it is also possible to utilize the oils-and-fats obtained by blending.

When an oil-and-fat containing SUS having a much crystal amount is crystallized by only one stage stirring crystallization, the crystal amount is too much and the viscosity of the crystal slurry is too high or the slurry is solidified, and the subsequent solid liquid separation becomes difficult. According to multistage fractionation of the present invention, since the crystal amount of the crystal slurry can be controlled so that the crystal slurry has flowability and thus can be transported with a pump, the conventional crystallizers which have previously been used in dry fractionation by stirring crystallization of palm oil or the like can be suitably utilized.

An stirring rate in a crystallization step is not particularly limited from the start of cooling to the time point when an oil temperature is lowered to a minimum crystallization temperature, but a relatively rapid rate is advantageous since cooling efficiency is enhanced and a cooling time can be shortened. From the time point when an oil temperature is lowered to a minimum crystallization temperature before press-filtration of the crystallized slurry, low rate stirring in such a range that a crystal is not settled is preferable in order to obtain a crystal having a low remaining liquid rate of filtrate components (entrainment) and high separation efficiency. In addition, the minimum crystallization temperature is a temperature at which an oil temperature becomes lowest during a crystallization step, and is usually around the temperature of a coolant used.

A preferable crystal amount of the crystal slurry to be subjected to press-filtration of the present invention is 10 to 20% by weight, preferably 10 to 15% by weight as a solid fat content. When the amount is less than 10% by weight, separation by press-filtration is good, but a fractionation yield of a crystal fraction is low, being not efficient. When the amount exceeds 20% by weight, a viscosity of the crystal slurry becomes high, and pump transportation to a press-filtration step becomes difficult, and at the same time, a remaining liquid rate of filtrate components into crystals (entrainment) in the press-filtration step becomes high, and separation accuracy is reduced, being not preferable. The solid fat content can be easily measured with NMR-pulse such as a solid fat measuring apparatus manufactured by BRUKER Co., and process control is easy.

In addition, it is preferable to raise a coolant temperature to a temperature which is higher than the original coolant temperature at crystallization by 2 to 4° C., after first stage stirring crystallization of a raw material oil-and-fat, and retain the temperature while stirring the oil-and-fat at a low speed in order to maintain the above-described crystal amount in a crystallization apparatus until completion of press-filtration. When this operation is not performed or the rise in a temperature is less than 2° C., crystal precipitation further progresses during holding the crystal slurry, and a rise in a viscosity or solidification of the crystal slurry occur, and therefore, this is not preferable. When the temperature is raised exceeding 4° C., partial dissolution of a crystal occurs, and at the same time, a decrease in separation efficiency during press-filtration also occurs, and therefore, this is also not preferable. After stirring crystallization at a second stage or thereafter, a rise in a coolant temperature is not particularly essential, and even when the temperature is not raised, further progress of crystal precipitation during holding the crystal slurry hardly occurs.

It is preferable to use a method of press-filtration such as filter press and membrane filter for separating an oil-and-fat into a crystal fraction and a filtrate fraction. Particularly, in order to obtain a fraction having a high SUS content, it is preferable that a remaining liquid rate of a filtrate into a crystal fraction is reduced by high pressure pressing at such a maximum pressure of 30 $Kg/cm^2$. In addition, in order to reduce the remaining liquid rate of a filtrate, it is advantageous that a thickness of a crystal cake after pressing is reduced as much as possible, and it is preferable that the thickness is reduced to 25 mm or less, more preferably 15 mm or less. In addition, when the following equation is utilized as a method of calculating the remaining liquid rate of a filtrate, the rate can be easily calculated, and even when the process is controlled by the calculated remaining liquid rate, there is no problem in separation accuracy control.

$$\text{Remaining liquid rate}(\%) = SUU \text{ content of crystal fraction}/SUU \text{ content of filtrate fraction} \times 100$$

(S: saturated fatty acid having 16 to 22 carbon atoms, U: unsaturated fatty acid having 18 carbon atoms)

An operation of stirring crystallization and press-filtration can also be repeated three times or more, but four or more times of repetition is not practical from the viewpoint of working efficiency of a crystallization facility and a press-filtration facility.

A crystallization time can be considerably shortened by adding a SUS-stable crystal flake in an amount of 1 to 50 ppm during cooling of an oil temperature to a minimum crystallization temperature by coolant or at the time point shortly after reaching to the minimum temperature, in stirring crystallization in the present invention. During cooling means the time point at which an oil temperature is cooled down to a range of between approximately +5° C. above the minimum temperature and the minimum temperature. Particularly, in stirring crystallization at a second stage or thereafter, the effect of shortening a crystallization time is large. As the SUS-stable crystal flake, a flake or powder such obtained can be suitably used, that an oil-and-fat having a SUS content of 60% by weight or more, preferably 70% by weight or more, further preferably 80% by weight or more is crystallized to give a block-like oil-and-fat with a rapid cooling kneading machine such as Onlator and Combinator, and then if necessary, the crystal is aged until a stable crystal is obtained, finally the block-like oil-and-fat is sliced or powdered to formulate into a flake or a powder. Desirably, it is preferable to use a stable crystal flake of an oil-and-fat having an SUS content of 60% by weight or more obtained from the raw material oil-and-fat for fractionation.

When an addition amount of the SUS-stable crystal flake is less than 1 ppm, a crystallization time tends to become too long. Conversely, when the amount exceeds 50 ppm, a desired crystal amount and viscosity cannot be retained from completion of crystallization to until finishing press-filtration, and press-filtration working becomes difficult due to an increase in the viscosity of the crystal slurry.

If necessary, an SUS-rich crystal fraction obtained by first stage of the dry fractionation in the present invention can be further fractionated by rising a temperature, partial dissolution, and filtration so that a high melting point portion is removed. Depending on the composition of a raw material oil-and-fat for fractionation, an SUS content of a crystal fraction is increased, and at the same time, the content of high melting point components such as trisaturated triglycerides and disaturated diglycerides are increased and, when the oil-and-fat is formulated into a cocoa butter substitute without removing these high melting point components, deterioration in tempering property and workability (increase in the viscosity during tempering) of chocolate and deterioration in melting speed in the mouth of chocolate may occur. In order to prevent such a problem in advance, it is possible to obtain an SUS-rich fraction from which a majority of high melting point components has been removed by a method of heating a pressed cake of a crystal fraction to raise its temperature and melt an oil-and-fat component having a melting point which is not higher than the melting point of the SUS component in a crystal, and thereby, remaining only a high melting point component as an unmolten component, and fractionating the component by filtration with a filter press or the like.

The fractionation method of the present invention can be suitably utilized in an oil-and-fat containing SUS having an SUS content of 30% by weight or more. In addition, it is preferable that an SUS content of an SUS-rich oil-and-fat obtained by the present invention is 60% by weight or more. When the SUS content is less than 60%, it is not preferable because there is a problem that the snappiness, and heat resistance and shape keeping property of chocolate are not good enough although the oil-and-fat can be used as a cocoa butter substitute. In order to formulate the oil-and-fat into a cocoa butter substitute having a snappiness and heat resistance and shape keeping property comparable to those of cocoa butter, it is desirable that the SUS content is 60% by weight or more, further preferably 70% by weight or more, most preferably 80% by weight or more.

The fractionation method of the present invention can be suitably utilized in fractionating an StOSt-rich oil-and-fat in which SUS substantially consists of StOSt (St: stearic acid, O: oleic acid). In dry fractionation by only one stage stirring crystallization of an oil-and-fat containing StOSt, there is a strong tendency that an increase in the viscosity and solidification of a crystal slurry are generated together with an increase in the crystal amount, and separation of an oil-and-fat into a crystal fraction and a filtrate fraction is difficult. By fractionating SUS by dividing crystallization and press-filtration of the present invention into multiple stages, efficient fractionation of a StOSt-rich oil-and-fat becomes possible.

The oil-and-fat containing StOSt in the present invention includes any one or more kinds of shea butter, sal fat, allanblackia fat, or an interesterified oil obtained by selectively introducing stearic acid into 1,3-positions of an oil-and-fat rich in oleic acid at a 2-position of triglycerides, and the present invention can be suitably utilized in fractionating these oils-and-fats. The interesterified oil obtained by selectively introducing a saturated fatty acid into 1,3-positions of an oil-and-fat rich in oleic acid at a 2-position of triglycerides includes an oil-and-fat obtained by interesterification with 1,3-position-specific lipase using, as a substrate, one or more kinds of oils-and-fats of high oleic sunflower oil, high oleic rapeseed oil, tea seed oil, olive oil, palm oil soft portion, or a fractionated low melting point portion of an interesterified oil obtained by selectively introducing stearic acid into 1,3-positions of these oils-and-fats, and stearic acid or a lower alcohol ester thereof, for example, an ethyl ester.

The present invention will be more specifically explained below by way of examples.

EXAMPLES

<Preparation of Interesterified Oil Obtained by Selectively Introducing Stearic Acid into 1,3-Positions of Oil-and-Fat Rich in Oleic Acid at 2-Position of Triglycerides>

Ethyl stearate and high oleic sunflower oil produced in Argentina were interesterified using, as a catalyst, lipase having 1,3-position specificity, and thereafter, an ethyl ester was distilled off to obtain an interesterified oil A. This interesterified oil had a StOSt content of 40.3%.

Example 1

<Fractionation at First Stage>

The interesterified oil A (75 Kg) was heated to 60° C. to completely melt, and placed in a crystallization tank having a diameter of 600 mm and a height of 500 mm equipped with a coolant jacket, and stirring and cooling were performed while a coolant of 31° C. was circulated in the coolant jacket. As a stirring blade, a paddle type blade having a width of 590 mm and a height of 260 mm was used, and cooling was performed at a stirring rate of 40 rpm while an oil temperature was cooled down from 60° C. to a minimum crystallization temperature of 31° C. After the temperature was cooled down to 31° C., the stirring rate was reduced to 10 rpm, and thereafter, the oil was held for 19 hours to complete crystallization. Thereafter, the coolant temperature was raised to 34° C., and a crystal slurry was transferred into a press-filtering machine with a pump while the slurry was held. Pressing was performed at 2.0 $Kg/cm^2/min$, the pressure was increased to 30 $Kg/cm^2$ for 15 minutes, and further, held at the same pressure for 15 minutes, and press-filtration was performed. As a pressed crystal fraction, AF1 in which StOSt content was concentrated to 68.3% was obtained with a fractionation yield of 30.5%. A remaining liquid rate of a filtrate in the crystal fraction was 30% or less, and thus, separation accuracy was good. The content of StOSt remaining in the filtrate fraction AL1 was 28.1%.

<Fractionation at Second Stage>

The filtrate fraction AL1 (75 Kg) obtained in the dry fractionation method at first stage was heated to 60° C. to completely melt, and placed into a crystallization tank having a diameter of 600 mm and a height of 500 mm equipped with a coolant jacket, and stirring and cooling were performed while a coolant of 26° C. was circulated in the coolant jacket. As a stirring blade, a paddle type blade having a width of 590 mm and a height of 260 mm was used, cooling was performed at a stirring rate of 40 rpm while an oil temperature was cooled down from 60° C. to a minimum crystallization temperature of 26° C., after cooled down to 26° C., the stirring rate was reduced to 10 rpm, and the oil was held for 48 hours to complete crystallization.

Thereafter, a crystal slurry was transferred into a press-filtering machine with a pump. Pressing was performed at 2.0 $Kg/cm^2/min$, the pressure was increased to 30 $Kg/cm^2$ for 15 minutes, and further, held at the same pressure for 15 minutes, and press-filtration was performed. As a crystal fraction, AF2 in which StOSt content was concentrated to 65.8% was obtained at a fractionation yield of 28.7%. This fractionation yield corresponds to 19.5% relative to a raw material for fractionation. The content of StOSt remaining in the filtrate fraction AL2 was 13.4%.

Example 2

In the fractionation at the second stage of Example 1, cooling was performed at a stirring rate of 40 rpm while an oil temperature was cooled down from 60° C. to a minimum crystallization temperature of 26° C., and after lowering to 26° C., the stirring rate was reduced to 10 rpm. Immediately after that, a stable crystal flake of StOSt (obtained by grinding a surface of Melano SS400 filled in a case manufactured by FUJI OIL CO., LTD. into a thin flake) was added at 10 ppm relative to a raw material oil-and-fat for fractionation, and the mixture was held for 26 hours to complete crystallization.

Thereafter, a crystal slurry was transferred into a press-filtering machine with a pump. Pressing was performed at 2.0 $Kg/cm^2/min$, the pressure was increased to 30 $Kg/cm^2$ for 15 minutes, and further, held at the same pressure for 15 minutes, and press-filtration was performed. As a crystal fraction, AF2 in which StOSt content was concentrated to 63.3% was obtained at a fractionation yield of 28.1%. This fractionation yield corresponds to 19.9% relative to a raw material for fractionation. The content of StOSt remaining in the filtrate fraction AL2 was 13.6%.

Comparative Example 1

For the purpose of fractionating the interesterified oil A used in Example 1 by only one stage stirring crystallization, stirring crystallization were performed in the same manner as in Example 1, except that the coolant temperature of the fractionation at the first stage of Example 1 was changed to 26° C. Good flowability was observed until SFC of a crystal slurry during crystallization became around 10%, but flowability almost disappeared at SFC of around 15% at which crystallization further progressed, and a crystal slurry which can be subjected to press-filtration thereafter was not obtained.

Comparative Example 2

In the fractionation at the first stage of Example 1, after completion of crystallization, a crystal slurry was held while the temperature was kept at 31° C. without raising the coolant temperature to 34° C. SFC of the crystal slurry immediately after completion of crystallization was 15.4%, thus, flowability was good, but crystallization further progressed in a crystallization apparatus during transfer into a press-filtering machine with a pump, thereafter, at 1 hour after completion of crystallization, the viscosity was rapidly increased as indicated by SFC of 24.5%, transportation into a press-filtering machine with a pump became impossible, and separation into a crystal fraction and a filtrate fraction became difficult. Since it became impossible to obtain the filtrate fraction, the fraction was not able to be subjected to fractionation at second stage.

Test results of Examples 1 and 2, and Comparative Examples 1 and 2 are shown in Table-1.

Test results thereafter are the following measurement values.

SFC: Solid fat content of crystal slurry (%)

SFC measuring method: Into a test tube having a length of 180 mm and a diameter of 10 mm was collected 3±0.3 g of a crystal slurry, this was inserted into a probe of SFC measuring apparatus manufactured by BRUKER Co. "minispec pc120 SFC measuring apparatus" as rapidly as possible, and SFC of the crystal slurry was measured by NMR-pulse. StOSt content, StOO content: Values measured by high performance liquid chromatography "%" means "% by weight" in all cases.

TABLE 1

| | | | SFC (%) | Fractionation yield (%) | StOSt content (%) | Remaining liquid rate (%) |
|---|---|---|---|---|---|---|
| | Raw material for fractionation | | | | 40.3 | |
| Example 1 | Fractionation at first stage | Crystal slurry | 14.0 | | | |
| | Crystallization temperature 31° C. | Crystal fraction | | 30.5 | 68.3 | 28.1 |
| | Crystallization time 21 hours | Filtrate fraction | | 69.5 | 28.1 | |
| | Fractionation at second stage | Crystal slurry | 18.7 | | | |
| | Crystallization temperature 26° C. | Crystal fraction | | 19.9 | 65.8 | 21.3 |
| | Crystallization time 50 hours | Filtrate fraction | | 49.6 | 13.4 | |
| Example 2 | Fractionation at first stage | Crystal slurry | 14.0 | | | |
| | Crystallization temperature 31° C. | Crystal fraction | | 30.5 | 68.3 | 28.1 |
| | Crystallization time 21 hours | Filtrate fraction | | 69.5 | 28.1 | |
| | Fractionation at second stage | Crystal slurry | 16.1 | | | |
| | Crystallization temperature 26° C. | Crystal fraction | | 19.5 | 63.3 | 21.6 |
| | Crystallization time 28 hours | Filtrate fraction | | 50.0 | 13.6 | |
| Comparative Example 1 | First stage fractionation | Crystal slurry | *15.0 | | | |
| | Crystallization temperature 26° C. | Crystal fraction | Not separable | | | |
| | Crystallization time 12 hours | Filtrate fraction | Not separable | | | |
| Comparative Example 2 | Fractionation at first stage | Crystal slurry | **15.4 | | | |
| | Crystallization temperature 31° C. | Crystal fraction | Not separable | | | |
| | Crystallization time 21 hours | Filtrate fraction | Not separable | | | |

*The viscosity was considerably increased at SFC 15.0%.

**Flowability was good at SFC 15.4%, but after 1 hour of press-filtering waiting, the viscosity was rapidly increased to 24.2%.

Crystallization temperature: Minimum crystallization temperature

Crystallization time: Time from the start of cooling to the completion of crystallization Remaining liquid rate (%): StOO content in crystal fraction/StOO content in filtrate fraction × 100

In Example 1, StOSt-rich crystal fractions respectively having a StOSt content of 68.3% and 65.8% were obtained from the raw material for fractionation at a yield of 30.5% and 19.9%. A high yield of 50.4% was obtained as a total of StOSt-rich oils-and-fats. Similarly, in Example 2, a high yield of 50.0% was obtained as a total of StOSt-rich oils-and-fats. On the other hand, when the crystal amount was increased to SFC 24.2% by one stage fractionation as in Comparative Example 1, rapid increase in viscosity of a crystal slurry occurred, and a crystal fraction and a filtrate fraction were not able to be separated.

Example 3

After the crystal fraction AF1 of fractionation at first stage obtained in Example 1 was roughly ground, the total amount was placed into a melting tank. The melting tank which was used was W 380 mm×L 380 mm×H 400 mm of a stainless tank in which a heating coil was equipped internally, and warm water at a constant temperature was able to be circulated in the interior of the coil. After the temperature was raised until the crystal fraction became 43.0° C., the fraction was held for a constant time (about 120 minutes) while stirring, and press-filtered with a filter press, and subjected to a solid liquid separation to remove a crystal in which high melting point glycerides were concentrated and to obtain a liquid AF1L at a yield of 91.5%.

The glycerides composition thereof is shown in Table-2.

TABLE 2

| | Glycerides composition (%) | | | |
|---|---|---|---|---|
| | StOSt | StOO | StStSt | StSt-DG |
| AF1 | 68.3 | 9.2 | 1.8 | 1.4 |
| AF1L | 69.3 | 9.6 | 0.9 | 0.7 |

The resulting AF1L and AF2 obtained in Example 1 were mixed to obtain an StOSt-rich oil-and-fat having a StOSt content of 67.0%. A fractionation yield of this oil-and-fat relative to the interesterified oil A was 47.4%.

Reference Example 1

The interesterified oil A was solvent fractionated by using normal hexane to obtain a fractionated middle melting point fraction having a StOSt content of 67.2% at a yield of 55.2%. The fractionation conditions were as follows: A high melting point fraction was removed by filtration after holding at an oil matter in a solvent of 30% at 15° C. for 30 minutes. Further, the filtrate fraction was held at −7° C. for 10 minutes and filtered to obtain a crystal portion. The crystal portion was washed with a solvent at a 3-fold weight equivalent of the oil-and-fat contained in the original filtrate fraction, and filtered again to obtain a middle melting point fraction as a crystal fraction thereof.

Reference Example 2

The interesterified oil A was heated to 50° C. or higher to completely melt, and allowed to stand at 23° C. to solidify, the resulting crystal was crushed and slurried, and then subjected to solid liquid separation by press-filtration. The resulting crystal fraction was heated to 50° C. or higher to completely melt, the interesterified oil A at a 1.5-fold weight equivalent which had been adjusted at 40° C. was mixed, and this was allowed to stand for 30 minutes, and press-filtered at a room temperature of 35° C. using a filter press. The resulting StOSt-rich crystal fraction was heated and molten by the same manner as in Example 3, and further, subjected to a solid liquid separation to remove a crystal in which high melting point glycerides were concentrated and to obtain a liquid having a StOSt content of 67.0%.

Table-3 shows a glyceride composition of the StOSt-rich oils-and-fats obtained in Example 3, and Reference Examples 1 and 2, and Table-4 shows SFC.

TABLE 3

| | Fractionation method | Fractionation yield (%) | StOSt | StOO | StStSt | SUS |
|---|---|---|---|---|---|---|
| Example 3 | Stirring crystallization method | 47.4 | 67.0 | 10.0 | 1.0 | 82.3 |
| Reference Example 1 | Solvent fractionation method | 55.2 | 67.2 | 7.7 | 1.0 | 84.6 |
| Reference Example 2 | Stationary crystallization method | 45.2 | 67.0 | 9.8 | 1.5 | 81.2 |

TABLE 4

| | SFC (Measured after stabilization at 26.7° C. for 40 hours, after rapid solidification) (%) | | | | | |
|---|---|---|---|---|---|---|
| | Fractonation method | 10° C. | 20° C. | 25° C. | 30° C. | 35° C. |
| Example 3 | Stirring crystallization method | 91.8 | 82.9 | 81.7 | 79.1 | 63.2 |
| Reference Example 1 | Solvent fractionation method | 93.7 | 87.3 | 86.2 | 83.7 | 67.6 |
| Reference Example 2 | Stationary crystallization method | 91.8 | 83.8 | 83.2 | 80.6 | 66.8 |

The StOSt-rich oil-and-fat according to a two stage stirring crystallization method of Example 3 showed a glycerides composition almost approximate to that of the StOSt-rich oil-and-fat obtained by the conventional solvent fractionation method of Reference Example 1 and the conventional stationary crystallization method of Reference Example 2, and was a high quality cocoa butter substitute in which SFC also showed a sharp melting property.

Industrial Applicability

The present invention relates to a dry oil-and-fat fractionation method by which a cocoa butter substitute suitably used in chocolate is obtained from an oil-and-fat containing SUS.

The invention claimed is:

1. A method of fractionating a SUS-rich oil-and-fat by multistage fractionation, comprising:

dry fractionating a raw material comprising an oil-and-fat comprising 30% by weight or more of an SUS by stirring crystallization and press-filtration to obtain a concentrated SUS in a crystal fraction and a remaining SUS in a filtrate fraction, and then dry fractionating the remaining SUS in the filtrate fraction by stirring crystallization and press-filtration to obtain a concentrated SUS-rich oil-and-fat comprising a content of SUS of 60% by weight or more, wherein the SUS is a 2-unsaturated, 1,3-disaturated triglyceride, the S is a saturated fatty acid having 16 to 22 carbon atoms, and the U is an unsaturated fatty acid having 18 carbon atoms.

2. The method according to claim 1, wherein the stirring crystallization produces a crystal amount of 10 to 20% by weight as a solid fat content of a crystal slurry to be subjected to the press-filtration.

3. The method according to claim 1, wherein the SUS is substantially StOSt, wherein St is stearic acid and O is oleic acid.

4. The method according to claim 1, wherein the oil-and-fat containing the SUS is one or more of an oil-and-fat selected from the group consisting of shea butter, sal fat, allanblackia fat, and an interesterified oil obtained by selectively introducing stearic acid into the 1,3-positions of an oil-and-fat rich in oleic acid at the 2-position of a triglyceride.

5. The method according to claim 2, wherein the SUS is substantially StOSt, wherein St is stearic acid and O is oleic acid.

6. The method according to claim 3, wherein the oil-and-fat containing StOSt is one or more of an oil-and-fat selected from the group consisting of shea butter, sal fat, allanblackia fat, and an interesterified oil obtained by selectively introducing stearic acid into the 1,3-positions of an oil-and-fat rich in oleic acid at the 2-position of a triglyceride.

7. The method according to claim 5, wherein the oil-and-fat containing StOSt is one or more of an oil-and-fat selected from the group consisting of shea butter, sal fat, allanblackia fat, and an interesterified oil obtained by selectively introducing stearic acid into the 1,3-positions of an oil-and-fat rich in oleic acid at the 2-position of a triglyceride.

* * * * *